(12) United States Patent
Friscia

(10) Patent No.: US 11,930,951 B2
(45) Date of Patent: Mar. 19, 2024

(54) VIBRATING BLANKET AND ALARM

(71) Applicant: Matthew Friscia, Franklin Lakes, NJ (US)

(72) Inventor: Matthew Friscia, Franklin Lakes, NJ (US)

( * ) Notice: Subject to any disclaimer, the term of this patent is extended or adjusted under 35 U.S.C. 154(b) by 0 days.

(21) Appl. No.: 17/152,837

(22) Filed: Jan. 20, 2021

(65) Prior Publication Data

US 2022/0225797 A1 Jul. 21, 2022

(51) Int. Cl.
*A47G 9/02* (2006.01)
*A47G 9/00* (2006.01)
(Continued)

(52) U.S. Cl.
CPC .............. *A47G 9/0223* (2013.01); *A47G 9/02* (2013.01); *A47G 9/0215* (2013.01); *A47G 9/1045* (2013.01); *A61B 5/6892* (2013.01); *A61M 21/02* (2013.01); *G04G 13/02* (2013.01); *A47G 2009/006* (2013.01); *A47G 2200/066* (2013.01); *A47G 2200/143* (2013.01); *A47G 2200/166* (2013.01); *A47G 2200/205* (2013.01); *A61B 5/0205* (2013.01); *A61B 5/4809* (2013.01);
(Continued)

(58) Field of Classification Search
CPC ................ A47G 9/0223; A47G 9/0215; A47G 2009/006; A47G 9/1045; A47G 9/0207; A47G 2200/066; A47G 2200/205; A47G 9/02; A47G 9/023; G04G 13/02; Y10S 5/94; Y10S 5/904; Y10S 5/915; A61B 5/68335; A61B 5/746; A61B 5/7405; A61B 5/4809; A61B 5/6892; A61B 5/02055; A61B 5/0205; A61B 5/02405; A61B 5/117; A61B 5/4806; A61B 5/4812; A47C 21/04; A47C 31/008; A47C 21/006; A61M 21/02; A61M 2021/0027; A61M 2021/0066
USPC ... 5/940, 482, 417, 904, 655, 915, 421, 485; 600/26
See application file for complete search history.

(56) References Cited

U.S. PATENT DOCUMENTS 4,005,703 A    2/1977  Rosen et al.
4,969,867 A *  11/1990 Cohen ................. A47G 9/0207
                                                    600/28
(Continued)

FOREIGN PATENT DOCUMENTS

CN    206933889 U  *  1/2018
JP    H06105735       *  4/1994  ............... A47G 9/02
(Continued)

OTHER PUBLICATIONS

"Interruption." Merriam-Webster, Merriam-Webster, www.merriam-webster.com/dictionary/interruption.*
(Continued)

*Primary Examiner* — Justin C Mikowski
*Assistant Examiner* — Madison Emanski
(74) *Attorney, Agent, or Firm* — McCarter & English, LLP

(57) ABSTRACT

A blanket having a vibrating element, heating element, sound generator, sound speaker and programmable wake-up alarm. A circuit electrically connects the programmable wake-up element with one or more of the vibrating element, heating element, sound generating element and sound speaker element to wake a sleeping person at a pre-set time by vibrations. A remote control can be used control the circuitry and the one or more elements of the blanket.

6 Claims, 2 Drawing Sheets

(51) Int. Cl.
    *A47G 9/10*         (2006.01)
    *A61B 5/00*         (2006.01)
    *A61M 21/00*       (2006.01)
    *A61M 21/02*       (2006.01)
    *G04G 13/02*       (2006.01)
    *A61B 5/0205*      (2006.01)

(52) U.S. Cl.
    CPC ............... *A61M 2021/0027* (2013.01); *A61M 2021/0066* (2013.01); *Y10S 5/904* (2013.01); *Y10S 5/915* (2013.01); *Y10S 5/94* (2013.01)

(56) References Cited

U.S. PATENT DOCUMENTS

| | | | | |
|---|---|---|---|---|
| 5,072,429 | A * | 12/1991 | Mair | A47G 9/1045 5/639 |
| 5,515,865 | A * | 5/1996 | Scanlon | A61B 5/6892 600/587 |
| 6,142,963 | A * | 11/2000 | Black | A47G 9/0223 5/915 |
| 6,170,602 | B1 | 1/2001 | Mann | |
| 7,417,530 | B1 | 8/2008 | Craig | |
| 2008/0024311 | A1* | 1/2008 | Mann | A61B 5/6892 340/573.1 |
| 2008/0106421 | A1* | 5/2008 | Adams | G16H 40/67 340/573.1 |
| 2008/0203080 | A1* | 8/2008 | Fung | A61F 7/034 219/528 |
| 2009/0089928 | A1* | 4/2009 | Kasbohm | A47G 9/0207 5/482 |
| 2014/0250595 | A1* | 9/2014 | Paperno | A47D 13/00 5/655 |
| 2014/0275742 | A1* | 9/2014 | Andrew | A41B 13/06 600/27 |
| 2015/0040315 | A1* | 2/2015 | Gersin | A61H 23/0263 5/417 |
| 2018/0085054 | A1* | 3/2018 | Miles | A47C 21/04 |
| 2020/0100682 | A1* | 4/2020 | Abreu | A61B 5/14553 |

FOREIGN PATENT DOCUMENTS

| | | | | |
|---|---|---|---|---|
| KR | 101959683 | * | 3/2019 | ........... A61H 39/007 |
| TW | M498547 U | * | 8/2014 | ................ A47G 9/02 |
| WO | WO 2019212901 | * | 4/2019 | ........... A61M 21/02 |
| WO | WO 2019212901 A1 | * | 11/2019 | ............. G16H 20/30 |

OTHER PUBLICATIONS

"Predetermined." The Free Dictionary, The Free Dictionary, https://www.thefreedictionary.com/predetermined.*

Ainyam, Raymond. "Can Microphones Be Used as Speakers? All You Need to Know!" Geek Musician, Apr. 11, 2020, https://geekmusician.com/can-microphones-be-used-as-speakers/#:~:text=what%20about%20microphones%3F-,Can%20microphones%20be%20used%20as%20speakers%3F,it%20receives%20an%20audio%20signal.*

* cited by examiner

VIBRATING BLANKET AND ALARM

BACKGROUND

Field

The present disclosure generally relates to blanket, and more particularly to a vibrating blanket and alarm, the blanket having one or more of a vibrating element, heating element, sound emitting element and programmable wake-up alarm.

Related Art

Blankets are well known and come in all shapes and sizes and are used to many ways including covering people during sleep.

SUMMARY

A blanket is provided with one or more of a vibrating element, heating element, sound emitting; element and programmable wake-up alarm. The blanket includes a circuit electrically connecting the programmable wake-up alarm with one or more of the vibrating element, heating element, sound emitting element. A remote control, or an application on a smartphone, can be used control the circuitry and the one or more elements of the blanket.

BRIEF DESCRIPTION OF THE DRAWINGS

The foregoing features will be apparent from the following Detailed Description, taken in connection with the accompanying drawings, in which.

DETAILED DESCRIPTION

Figure 1:
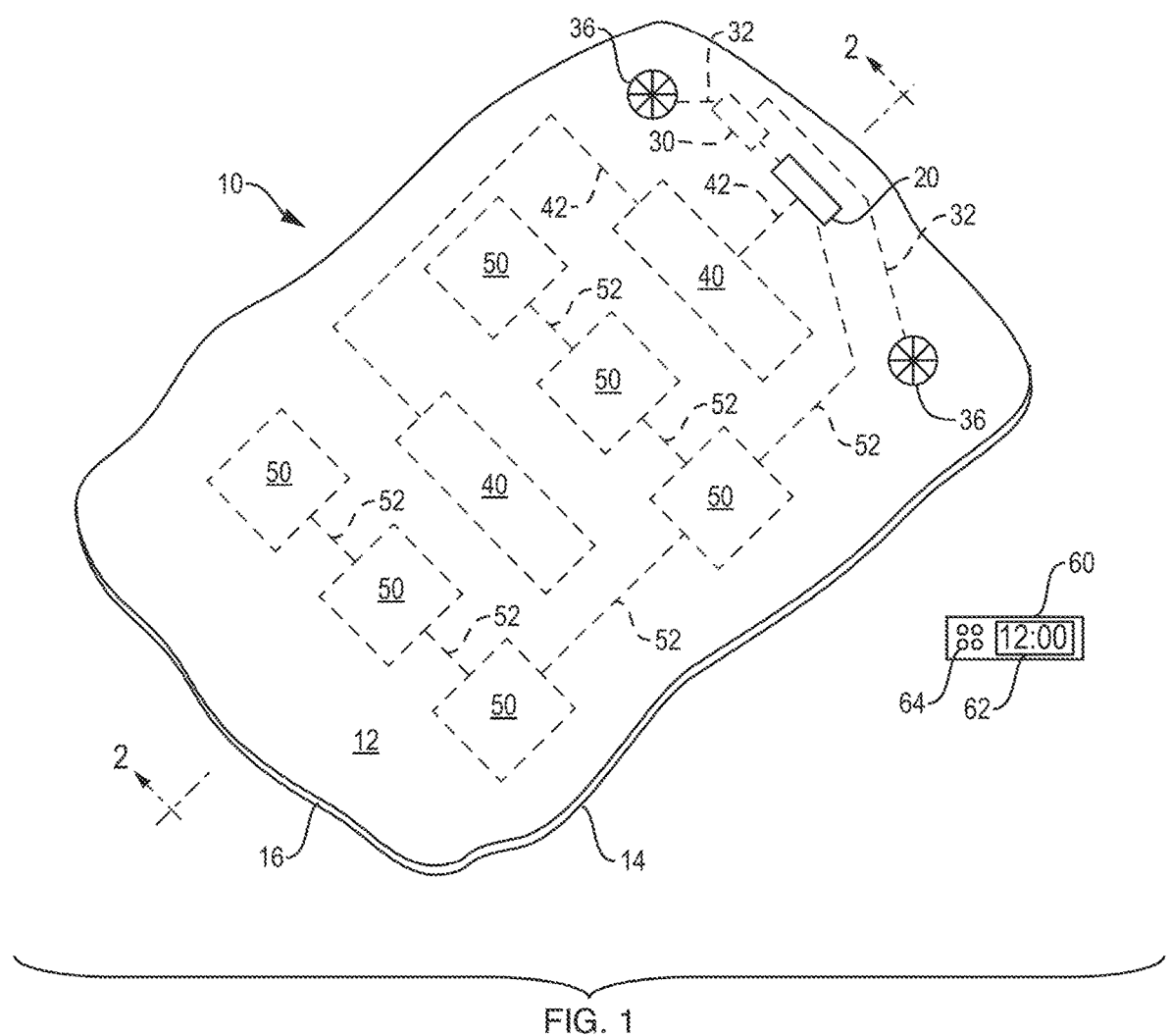
FIG. 1 is a perspective view showing a blanket with a controller, vibrating elements, heating elements, and sound emitting elements.

A vibrating blanket and alarm is shown in FIG. 1. The blanket, generally indicated at 10, could be of any configuration, size or shape. It can be used to cover a person while the person is sleeping, or it can be otherwise used as blankets are used. It could be soft, with padding inside, and it could be plush on the outside.

Figure 2:
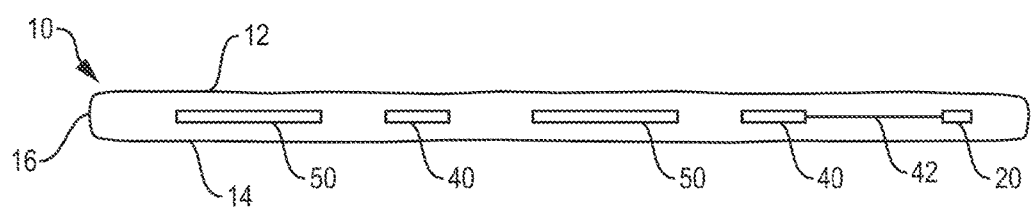
FIG. 2 is a cross sectional view of the blanket shown in FIG. 1 taken along line 2-2.

As shown in FIGS. 1 and 2, the blanket includes a top 12 and a bottom 14. The top 12 and bottom 14 can be attached together, or the top 12 and bottom 14 can be connected to a sidewall 16 that extends about the perimeter of the blanket 10.

Figure 3:
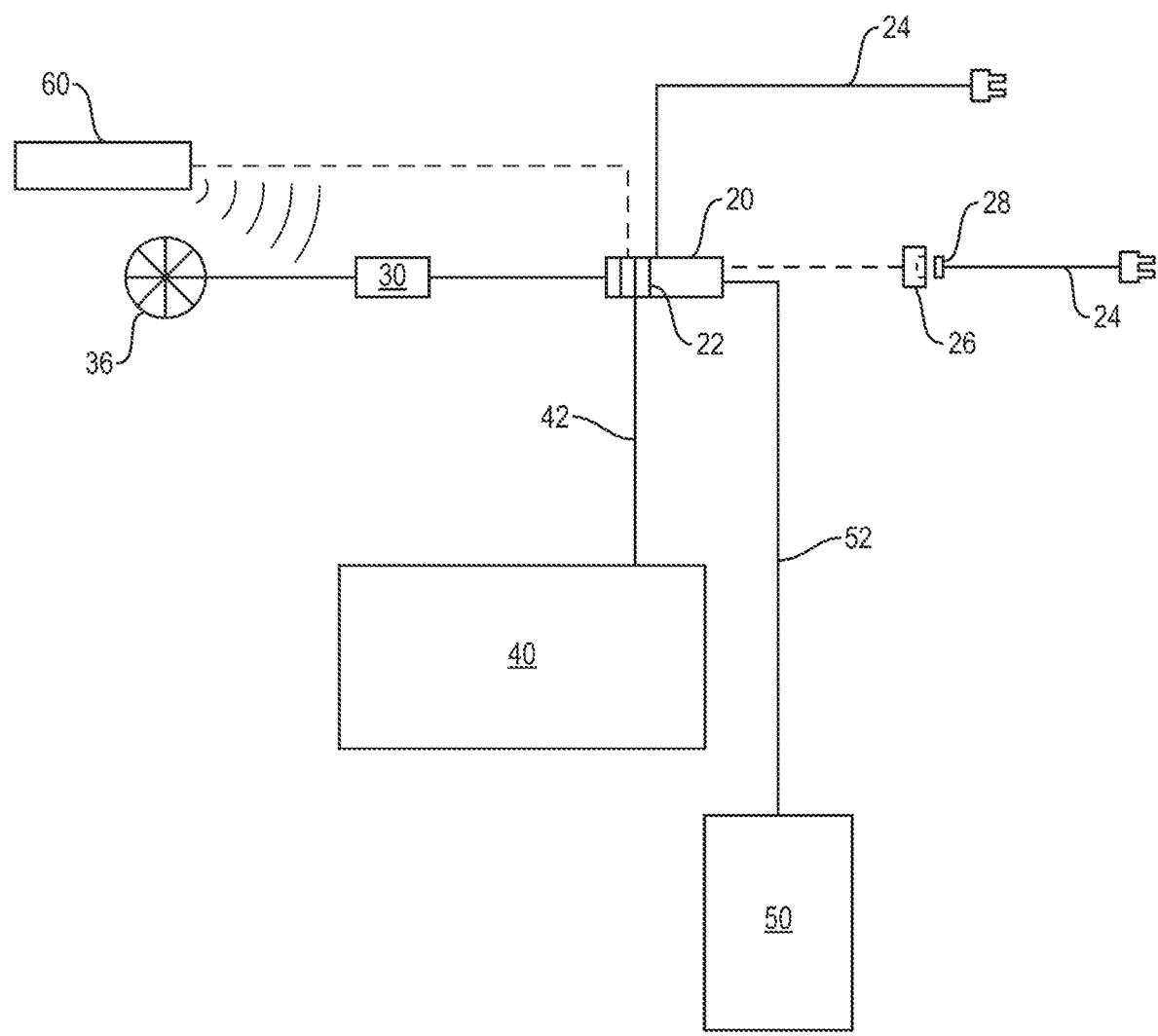
FIG. 3 is a schematic diagram of a circuit for the vibrating blanket and alarm.

Referring to FIGS. 1-3, the blanket 10 includes one or more or more vibrating elements 50, and can include one or more heating elements 40. The blanket 10 also includes a sound emitting element that can include a sound generator 30 and sound speaker 36. The one or more vibrating elements 50. heating elements 49 and sound speaker 36 are all positioned within or partially within the blanket 10. The sound generator 30 can be positioned within the blanket, as shown, or it can be exterior to the blanket. The blanket 10 can include a controller 20 electrically connected to the vibrating element 50, heating element 40, and sound generator 30 for controlling these items. The controller 20 can be positioned within the blanket 10, or exterior to the blanket 10, and can powered with an electrical cord that is plugged into an outlet, or it can be battery powered. If the controller 20 is positioned within the blanket 10, the battery or batteries 22 can be charged by a cord extending from the controller 20 to the exterior of the blanket 10, or the controller 20 can be proximate the exterior of the blanket 10 and a charging cord 24 can be plugged into the controller 20, through a top wall 12, bottom wall 14 or sidewall 16, at one end and into an outlet at the other end. The controller 20 can also be inductively charged by placing the blanket 10, or a portion thereof with induction charging circuitry 26, on an induction charging apparatus 28. Alternatively, the controller 20 can have a battery compartment that is accessed from outside the blanket for receiving batteries 22 and/or replacement batteries 22.

The controller 20 may be accessed and actuated manually from the exterior of the blanket 10 or remotely. The controller 20 can include a control panel with controls that are accessible from the exterior of the blanket 10. It can be covered by a flap of the blanket 10 to cover the controller 20 when not in use and maintain the uniformity of the sides and/or edge of the blanket 10.

Alternatively, the controller 20 can be distributed such that each of the vibrating element, the heating element, the sound emitting element incorporate distributed controls for each of said elements that are directly operated by a remote control 60 exterior of the blanket 110. The remote control 60 could be wired or wireless. The controller 20, or distributed controls, can be operated by a dedicated remote control 60 which could have include a clock 62 and controls 64 that can be manipulated by a user. Alternatively, the controller 20, or distributed controls, can be operated through a software application on a smartphone 70. The controller 20, or distributed controls, can include Bluetooth (Bluetooth is a registered trademark of Bluetooth SIG, Inc.) technology or another communication interface to receive communications from the remote control 60 or smartphone 70.

The controller 20, or distributed controls, can control the length of time a vibrating element 50 is actuated, and the level of intensity of the vibration. The one or more vibrating elements 50 can be controlled to turn on or off at predetermined times. The controller 20, or distributed controls, can also control the length of time a heating element 40 is actuated and the level or amount of heat generated. The one or more heating elements 40 can be turned on or off at predetermined times. The controller 20, or distributed controls, can also control the actuation of the sound generator 30 or sound speaker 36 including the sound input and the volume. The one or more sound speakers 36 can be turned on or off at predetermined times. All of these elements, and the controller, or distributed controls, can be controlled and programed through a software application on a smartphone.

The vibration element or elements 50 can be any vibration mechanism or vibration generator known in the art and suitable for inclusion in a blanket such as an oscillator with a motor and a built-in imbalance. For example, a vibration mechanism from a vibrating plush toy could be used. The heating element or elements 40 can be any heating element known in the art and suitable for inclusion in a blanket such as heating element from a heating pad or heated blanket. The sound emitting element can be any music playing mechanism suitable for inclusion into a blanket. The sound emitting element can comprise one or more speakers, such as Bluetooth enabled speakers, that can play music from a smartphone.

As shown in FIG. 3, a circuit 80 can be used with the blanket 10. The circuitry 80 can include a controller 20, optionally with batteries 22, wiring 31 to sound generating element 30, wiring 32 to sound speaker element 36, wiring 42 to heating element 40, and wiring 52 to vibrating element 50. The settings for each element, including the intensity or volume, and the duration, can be controlled from the controller 20, or from a remote control 60 or by a software application on a smartphone 70. The circuit 80 can be programmed, or set, to turn on or turn off one or more elements at a specific time or after a specific duration of time after actuation. Additionally, each of the elements can be programmed, or set, to turn on a specific element at a scheduled time so that the blanket 10 functions as a wake-up alarm that can be set to start vibrating, heating or emitting sound, or a combination thereof, at a particular time to wake-up or otherwise notify a user in a manner chosen by the user, such as vibration, heat or sound or a combination. For example, one could use the blanket and turn on vibration and heat for a period of time to ease one to sleep, and then to set a sound or music alarm in the morning to wake up the user. Other combinations or activating and deactivating elements, as desired, can be set by a user.

It will be apparent to one skilled in the art that various changes and modifications can be made to the disclosure herein therein without departing from the spirit and scope thereof.

What is claimed is:

1. A plush vibrating blanket with a wake-up alarm comprising:
   a blanket having a top surface and a bottom surface;
   one or more adjustable vibration generators positioned within the blanket;
   speakers within the blanket;
   a controller within the blanket, the controller electrically connected with the one or more vibration generators, the controller actuable to turn the one or more vibration generators on and off and for controlling the intensity of the vibrations,
   the controller electrically connected with the speakers, the controller actuable to turn the speakers on and off and for controlling volume of the speakers; and
   a wireless remote control for programing the controller to change the intensity and to turn on and off the one or more vibration generators, and the remote control programing the controller to turn on the speakers at a specific, pre-set time, to wake up a user from sleep.

2. The blanket of claim 1 wherein the remote control is programmed to turn on the one or more vibration generators a specific time, and to increase the intensity of the vibrations of the vibration generators over time after the vibration generators are turned on to wake up a user from sleep.

3. The blanket of claim 1 further comprising one or more heaters in the blanket.

4. The blanket of claim 1 further comprising a software application downloadable to a smartphone to control the vibrating generator and speakers.

5. The blanket of claim 4 wherein the user can go to sleep with the one or more vibration generators actuated, the vibration generators programed via the smartphone to turn off after a pre-set vibration duration, and the speakers programmed to play music at a specific time to awaken the user.

6. The blanket of claim 5 further comprising one or more heaters programmable to turn off after a pre-set heat duration.

* * * * *